United States Patent
Budiman et al.

(10) Patent No.: US 8,219,173 B2
(45) Date of Patent: Jul. 10, 2012

(54) OPTIMIZING ANALYTE SENSOR CALIBRATION

(75) Inventors: Erwin Satrya Budiman, Fremont, CA (US); Wesley Scott Harper, Milpitas, CA (US); Timothy Christian Dunn, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 932 days.

(21) Appl. No.: 12/242,823

(22) Filed: Sep. 30, 2008

(65) Prior Publication Data

US 2010/0081909 A1  Apr. 1, 2010

(51) Int. Cl.
A61B 5/05 (2006.01)
(52) U.S. Cl. .......... 600/345; 600/347; 600/365
(58) Field of Classification Search .......... 600/345–347, 600/365; 435/4; 422/50; 204/403.01–403.15
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |

(Continued)

FOREIGN PATENT DOCUMENTS

DE  4401400  7/1995

(Continued)

OTHER PUBLICATIONS

PCT Application No. PCT/US2009/058895, International Search Report and Written Opinion of the International Searching Authority mailed Nov. 20, 2009.

(Continued)

*Primary Examiner* — Michael Kahelin
*Assistant Examiner* — Michael D'Angelo
(74) *Attorney, Agent, or Firm* — Jackson & Co., LLP

(57) ABSTRACT

Method and apparatus for optimizing analyte sensor calibration including receiving a current blood glucose measurement, retrieving a time information for an upcoming scheduled calibration event for calibrating an analyte sensor, determining temporal proximity between the current blood glucose measurement and the retrieved time information for the upcoming calibration event, initiating a calibration routine to calibrate the analyte sensor when the determined temporal proximity is within a predetermined time period, and overriding the upcoming scheduled calibration event using the current blood glucose measurement are provided.

20 Claims, 4 Drawing Sheets

U.S. PATENT DOCUMENTS

| | | |
|---|---|---|
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A * | 4/1996 | Bocker et al. ............... 600/322 |
| 5,509,410 A | 4/1996 | Hill et al. |
| 5,514,718 A | 5/1996 | Lewis et al. |
| 5,531,878 A | 7/1996 | Vadgama et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,733,259 A | 3/1998 | Valcke et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |

| | | | |
|---|---|---|---|
| 6,741,877 B1 | 5/2004 | Shults et al. | |
| 6,746,582 B2 | 6/2004 | Heller et al. | |
| 6,758,810 B2 | 7/2004 | Lebel et al. | |
| 6,770,030 B1 | 8/2004 | Schaupp et al. | |
| 6,790,178 B1 | 9/2004 | Mault et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,862,465 B2 | 3/2005 | Shults et al. | |
| 6,873,268 B2 | 3/2005 | Lebel et al. | |
| 6,881,551 B2 | 4/2005 | Heller et al. | |
| 6,892,085 B2 | 5/2005 | McIvor et al. | |
| 6,895,263 B2 * | 5/2005 | Shin et al. | 600/316 |
| 6,895,265 B2 | 5/2005 | Silver | |
| 6,931,327 B2 | 8/2005 | Goode, Jr. et al. | |
| 6,932,894 B2 | 8/2005 | Mao et al. | |
| 6,936,006 B2 | 8/2005 | Sabra | |
| 6,950,708 B2 | 9/2005 | Bowman, IV et al. | |
| 6,958,705 B2 | 10/2005 | Lebel et al. | |
| 6,968,294 B2 | 11/2005 | Gutta et al. | |
| 6,971,274 B2 | 12/2005 | Olin | |
| 6,974,437 B2 | 12/2005 | Lebel et al. | |
| 6,990,366 B2 | 1/2006 | Say et al. | |
| 6,997,907 B2 | 2/2006 | Safabash et al. | |
| 6,998,247 B2 | 2/2006 | Monfre et al. | |
| 7,003,336 B2 | 2/2006 | Holker et al. | |
| 7,003,340 B2 | 2/2006 | Say et al. | |
| 7,003,341 B2 | 2/2006 | Say et al. | |
| 7,022,072 B2 | 4/2006 | Fox et al. | |
| 7,024,245 B2 | 4/2006 | Lebel et al. | |
| 7,029,444 B2 * | 4/2006 | Shin et al. | 600/365 |
| 7,041,068 B2 | 5/2006 | Freeman et al. | |
| 7,052,483 B2 | 5/2006 | Wojcik | |
| 7,056,302 B2 | 6/2006 | Douglas | |
| 7,074,307 B2 | 7/2006 | Simpson et al. | |
| 7,081,195 B2 | 7/2006 | Simpson et al. | |
| 7,098,803 B2 | 8/2006 | Mann et al. | |
| 7,108,778 B2 | 9/2006 | Simpson et al. | |
| 7,110,803 B2 | 9/2006 | Shults et al. | |
| 7,113,821 B1 | 9/2006 | Sun et al. | |
| 7,134,999 B2 | 11/2006 | Brauker et al. | |
| 7,136,689 B2 | 11/2006 | Shults et al. | |
| 7,171,274 B2 | 1/2007 | Starkweather et al. | |
| 7,190,988 B2 | 3/2007 | Say et al. | |
| 7,192,450 B2 | 3/2007 | Brauker et al. | |
| 7,198,606 B2 | 4/2007 | Boecker et al. | |
| 7,226,978 B2 | 6/2007 | Tapsak et al. | |
| 7,258,673 B2 | 8/2007 | Racchini et al. | |
| 7,267,665 B2 | 9/2007 | Steil et al. | |
| 7,276,029 B2 | 10/2007 | Goode, Jr. et al. | |
| 7,299,082 B2 | 11/2007 | Feldman et al. | |
| 7,310,544 B2 | 12/2007 | Brister et al. | |
| 7,317,938 B2 | 1/2008 | Lorenz et al. | |
| 7,335,294 B2 | 2/2008 | Heller et al. | |
| 7,354,420 B2 | 4/2008 | Steil et al. | |
| 7,364,592 B2 | 4/2008 | Carr-Brendel et al. | |
| 7,366,556 B2 | 4/2008 | Brister et al. | |
| 7,379,765 B2 | 5/2008 | Petisce et al. | |
| 7,402,153 B2 | 7/2008 | Steil et al. | |
| 7,424,318 B2 | 9/2008 | Brister et al. | |
| 7,460,898 B2 | 12/2008 | Brister et al. | |
| 7,467,003 B2 | 12/2008 | Brister et al. | |
| 7,471,972 B2 | 12/2008 | Rhodes et al. | |
| 7,494,465 B2 | 2/2009 | Brister et al. | |
| 7,497,827 B2 | 3/2009 | Brister et al. | |
| 7,499,002 B2 | 3/2009 | Blasko et al. | |
| 7,519,408 B2 | 4/2009 | Rasdal et al. | |
| 7,547,281 B2 | 6/2009 | Hayes et al. | |
| 7,569,030 B2 | 8/2009 | Lebel et al. | |
| 7,583,990 B2 | 9/2009 | Goode, Jr. et al. | |
| 7,591,801 B2 | 9/2009 | Brauker et al. | |
| 7,599,726 B2 | 10/2009 | Goode, Jr. et al. | |
| 7,613,491 B2 | 11/2009 | Boock et al. | |
| 7,615,007 B2 | 11/2009 | Shults et al. | |
| 7,618,369 B2 | 11/2009 | Hayter et al. | |
| 7,630,748 B2 | 12/2009 | Budiman | |
| 7,632,228 B2 | 12/2009 | Brauker et al. | |
| 7,699,964 B2 | 4/2010 | Feldman et al. | |
| 7,774,145 B2 | 8/2010 | Brauker et al. | |
| 7,778,680 B2 | 8/2010 | Goode, Jr. et al. | |
| 7,826,981 B2 | 11/2010 | Goode, Jr. et al. | |
| 7,905,833 B2 | 3/2011 | Brister et al. | |
| 7,914,450 B2 | 3/2011 | Goode, Jr. et al. | |
| 2001/0041831 A1 | 11/2001 | Starkweather et al. | |
| 2002/0019022 A1 | 2/2002 | Dunn et al. | |
| 2002/0042090 A1 | 4/2002 | Heller et al. | |
| 2002/0103499 A1 | 8/2002 | Perez et al. | |
| 2002/0106709 A1 | 8/2002 | Potts et al. | |
| 2002/0128594 A1 | 9/2002 | Das et al. | |
| 2002/0161288 A1 | 10/2002 | Shin et al. | |
| 2002/0169635 A1 | 11/2002 | Shillingburg | |
| 2002/0193679 A1 | 12/2002 | Malave et al. | |
| 2003/0004403 A1 | 1/2003 | Drinan et al. | |
| 2003/0023317 A1 | 1/2003 | Brauker et al. | |
| 2003/0032874 A1 | 2/2003 | Rhodes et al. | |
| 2003/0042137 A1 | 3/2003 | Mao et al. | |
| 2003/0050546 A1 | 3/2003 | Desai et al. | |
| 2003/0065308 A1 | 4/2003 | Lebel et al. | |
| 2003/0100821 A1 | 5/2003 | Heller et al. | |
| 2003/0125612 A1 | 7/2003 | Fox et al. | |
| 2003/0130616 A1 | 7/2003 | Steil et al. | |
| 2003/0134347 A1 | 7/2003 | Heller et al. | |
| 2003/0168338 A1 | 9/2003 | Gao et al. | |
| 2003/0176933 A1 | 9/2003 | Lebel et al. | |
| 2003/0187338 A1 | 10/2003 | Say et al. | |
| 2003/0191377 A1 | 10/2003 | Robinson et al. | |
| 2003/0199790 A1 | 10/2003 | Boecker et al. | |
| 2003/0208113 A1 | 11/2003 | Mault et al. | |
| 2003/0212317 A1 | 11/2003 | Kovatchev et al. | |
| 2003/0212379 A1 | 11/2003 | Bylund et al. | |
| 2003/0216630 A1 | 11/2003 | Jersey-Willuhn et al. | |
| 2003/0217966 A1 | 11/2003 | Tapsak et al. | |
| 2004/0010207 A1 | 1/2004 | Flaherty et al. | |
| 2004/0011671 A1 | 1/2004 | Shults et al. | |
| 2004/0039298 A1 | 2/2004 | Abreu | |
| 2004/0040840 A1 | 3/2004 | Mao et al. | |
| 2004/0045879 A1 | 3/2004 | Shults et al. | |
| 2004/0064068 A1 | 4/2004 | DeNuzzio et al. | |
| 2004/0099529 A1 | 5/2004 | Mao et al. | |
| 2004/0106858 A1 | 6/2004 | Say et al. | |
| 2004/0122353 A1 | 6/2004 | Shahmirian et al. | |
| 2004/0133164 A1 | 7/2004 | Funderburk et al. | |
| 2004/0138588 A1 | 7/2004 | Saikley et al. | |
| 2004/0146909 A1 | 7/2004 | Duong et al. | |
| 2004/0152622 A1 | 8/2004 | Keith et al. | |
| 2004/0167801 A1 | 8/2004 | Say et al. | |
| 2004/0171921 A1 | 9/2004 | Say et al. | |
| 2004/0176672 A1 | 9/2004 | Silver et al. | |
| 2004/0186362 A1 | 9/2004 | Brauker et al. | |
| 2004/0186365 A1 | 9/2004 | Jin et al. | |
| 2004/0193025 A1 | 9/2004 | Steil et al. | |
| 2004/0193090 A1 | 9/2004 | Lebel et al. | |
| 2004/0197846 A1 | 10/2004 | Hockersmith et al. | |
| 2004/0199059 A1 | 10/2004 | Brauker et al. | |
| 2004/0204687 A1 | 10/2004 | Mogensen et al. | |
| 2004/0208780 A1 | 10/2004 | Faries, Jr. et al. | |
| 2004/0225338 A1 | 11/2004 | Lebel et al. | |
| 2004/0236200 A1 | 11/2004 | Say et al. | |
| 2004/0254433 A1 | 12/2004 | Bandis et al. | |
| 2004/0263354 A1 | 12/2004 | Mann et al. | |
| 2004/0267300 A1 | 12/2004 | Mace | |
| 2005/0003470 A1 | 1/2005 | Nelson et al. | |
| 2005/0004439 A1 | 1/2005 | Shin et al. | |
| 2005/0004494 A1 | 1/2005 | Perez et al. | |
| 2005/0010087 A1 | 1/2005 | Banet et al. | |
| 2005/0010269 A1 | 1/2005 | Lebel et al. | |
| 2005/0016276 A1 | 1/2005 | Guan et al. | |
| 2005/0027177 A1 | 2/2005 | Shin et al. | |
| 2005/0031689 A1 | 2/2005 | Shults et al. | |
| 2005/0038332 A1 | 2/2005 | Saidara et al. | |
| 2005/0043598 A1 | 2/2005 | Goode, Jr. et al. | |
| 2005/0090607 A1 | 4/2005 | Tapsak et al. | |
| 2005/0096511 A1 | 5/2005 | Fox et al. | |
| 2005/0096512 A1 | 5/2005 | Fox et al. | |
| 2005/0112169 A1 | 5/2005 | Brauker et al. | |
| 2005/0113653 A1 | 5/2005 | Fox et al. | |

| | | |
|---|---|---|
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0272652 A1 | 12/2006 | Stocker et al. |
| 2006/0281985 A1 | 12/2006 | Ward et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0232877 A1 | 10/2007 | He |
| 2007/0235331 A1 | 10/2007 | Simpson et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0154513 A1 | 6/2008 | Kovatchev et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0006034 A1 | 1/2009 | Hayter et al. |

| | | | | | | |
|---|---|---|---|---|---|---|
| 2009/0012379 A1 | 1/2009 | Goode et al. | | EP | 0320109 | 6/1989 |
| 2009/0018424 A1 | 1/2009 | Kamath et al. | | EP | 0353328 | 2/1990 |
| 2009/0030294 A1 | 1/2009 | Petisce et al. | | EP | 0390390 | 10/1990 |
| 2009/0033482 A1 | 2/2009 | Hayter et al. | | EP | 0396788 | 11/1990 |
| 2009/0036747 A1 | 2/2009 | Hayter et al. | | EP | 0286118 | 1/1995 |
| 2009/0036758 A1 | 2/2009 | Brauker et al. | | EP | 1048264 | 11/2000 |
| 2009/0036760 A1 | 2/2009 | Hayter | | WO | WO-96/25089 | 8/1996 |
| 2009/0036763 A1 | 2/2009 | Brauker et al. | | WO | WO-96/35370 | 11/1996 |
| 2009/0043181 A1 | 2/2009 | Brauker et al. | | WO | WO-98/35053 | 8/1998 |
| 2009/0043182 A1 | 2/2009 | Brauker et al. | | WO | WO-99/56613 | 11/1999 |
| 2009/0043525 A1 | 2/2009 | Brauker et al. | | WO | WO-00/49940 | 8/2000 |
| 2009/0043541 A1 | 2/2009 | Brauker et al. | | WO | WO-00/59370 | 10/2000 |
| 2009/0043542 A1 | 2/2009 | Brauker et al. | | WO | WO-00/74753 | 12/2000 |
| 2009/0045055 A1 | 2/2009 | Rhodes et al. | | WO | WO-00/78992 | 12/2000 |
| 2009/0055149 A1 | 2/2009 | Hayter et al. | | WO | WO-01/52935 | 7/2001 |
| 2009/0062633 A1 | 3/2009 | Brauker et al. | | WO | WO-01/54753 | 8/2001 |
| 2009/0062635 A1 | 3/2009 | Brauker et al. | | WO | WO-02/16905 | 2/2002 |
| 2009/0062767 A1 | 3/2009 | VanAntwerp et al. | | WO | WO-02/058537 | 8/2002 |
| 2009/0063402 A1 | 3/2009 | Hayter | | WO | WO-03/076893 | 9/2003 |
| 2009/0076356 A1 | 3/2009 | Simpson et al. | | WO | WO-03/082091 | 10/2003 |
| 2009/0076360 A1 | 3/2009 | Brister et al. | | WO | WO-03/085372 | 10/2003 |
| 2009/0076361 A1 | 3/2009 | Kamath et al. | | WO | WO-2004/060455 | 7/2004 |
| 2009/0099436 A1 | 4/2009 | Brister et al. | | WO | WO-2004/061420 | 7/2004 |
| 2009/0105636 A1 | 4/2009 | Hayter et al. | | WO | WO-2005/041766 | 5/2005 |
| 2009/0124877 A1 | 5/2009 | Goode, Jr. | | WO | WO-2005/065542 | 7/2005 |
| 2009/0124878 A1 | 5/2009 | Goode et al. | | WO | WO-2005/089103 | 9/2005 |
| 2009/0124879 A1 | 5/2009 | Brister et al. | | WO | WO-2006/024671 | 3/2006 |
| 2009/0124964 A1 | 5/2009 | Leach et al. | | WO | WO-2006/079114 | 7/2006 |
| 2009/0131768 A1 | 5/2009 | Simpson et al. | | WO | WO-2006/086423 | 8/2006 |
| 2009/0131769 A1 | 5/2009 | Leach et al. | | WO | WO-2006/118947 | 11/2006 |
| 2009/0131776 A1 | 5/2009 | Simpson et al. | | WO | WO-2007/016399 | 2/2007 |
| 2009/0131777 A1 | 5/2009 | Simpson et al. | | WO | WO-2007/027788 | 3/2007 |
| 2009/0137886 A1 | 5/2009 | Shariati et al. | | WO | WO-2007/041069 | 4/2007 |
| 2009/0137887 A1 | 5/2009 | Shariati et al. | | WO | WO-2007/041070 | 4/2007 |
| 2009/0143659 A1 | 6/2009 | Li et al. | | WO | WO-2007/041072 | 4/2007 |
| 2009/0143660 A1 | 6/2009 | Brister et al. | | WO | WO-2007/041248 | 4/2007 |
| 2009/0156919 A1 | 6/2009 | Brister et al. | | WO | WO-2007/056638 | 5/2007 |
| 2009/0156924 A1 | 6/2009 | Shariati et al. | | WO | WO-2007/101223 | 9/2007 |
| 2009/0163790 A1 | 6/2009 | Brister et al. | | WO | WO-2007/115094 | 10/2007 |
| 2009/0163791 A1 | 6/2009 | Brister et al. | | WO | WO-2007/120363 | 10/2007 |
| 2009/0164190 A1 | 6/2009 | Hayter | | WO | WO-2007/126444 | 11/2007 |
| 2009/0164239 A1 | 6/2009 | Hayter et al. | | WO | WO-2007/053832 | 12/2007 |
| 2009/0164251 A1 | 6/2009 | Hayter | | WO | WO-2007/143225 | 12/2007 |
| 2009/0178459 A1 | 7/2009 | Li et al. | | WO | WO-2008/021913 | 2/2008 |
| 2009/0182217 A1 | 7/2009 | Li et al. | | WO | WO-2008/042760 | 4/2008 |
| 2009/0192366 A1 | 7/2009 | Mensinger et al. | | WO | WO-2008/052057 | 5/2008 |
| 2009/0192380 A1 | 7/2009 | Shariati et al. | | WO | WO-2008/128210 | 10/2008 |
| 2009/0192722 A1 | 7/2009 | Shariati et al. | | WO | WO-2008/130896 | 10/2008 |
| 2009/0192724 A1 | 7/2009 | Brauker et al. | | WO | WO-2008/130897 | 10/2008 |
| 2009/0192745 A1 | 7/2009 | Kamath et al. | | WO | WO-2008/130898 | 10/2008 |
| 2009/0192751 A1 | 7/2009 | Kamath et al. | | WO | WO-2008/143943 | 11/2008 |
| 2009/0198118 A1 | 8/2009 | Hayter et al. | | WO | WO-2009/018058 | 2/2009 |
| 2009/0203981 A1 | 8/2009 | Brauker et al. | | WO | WO-2009/086216 | 7/2009 |
| 2009/0204341 A1 | 8/2009 | Brauker et al. | | WO | WO-2009/096992 | 8/2009 |
| 2009/0216103 A1 | 8/2009 | Brister et al. | | WO | WO-2009/097594 | 8/2009 |
| 2009/0240120 A1 | 9/2009 | Mensinger et al. | | | | |
| 2009/0240128 A1 | 9/2009 | Mensinger et al. | | | | |
| 2009/0240193 A1 | 9/2009 | Mensinger et al. | | | | |
| 2009/0242399 A1 | 10/2009 | Kamath et al. | | | | |
| 2009/0242425 A1 | 10/2009 | Kamath et al. | | | | |
| 2009/0247855 A1 | 10/2009 | Boock et al. | | | | |
| 2009/0247856 A1 | 10/2009 | Boock et al. | | | | |
| 2009/0247857 A1 | 10/2009 | Harper et al. | | | | |
| 2009/0287073 A1 | 11/2009 | Boock et al. | | | | |
| 2009/0287074 A1 | 11/2009 | Shults et al. | | | | |
| 2009/0299155 A1 | 12/2009 | Yang et al. | | | | |
| 2009/0299156 A1 | 12/2009 | Simpson et al. | | | | |
| 2009/0299162 A1 | 12/2009 | Brauker et al. | | | | |
| 2009/0299276 A1 | 12/2009 | Brauker et al. | | | | |
| 2010/0057040 A1 | 3/2010 | Hayter | | | | |
| 2010/0057041 A1 | 3/2010 | Hayter | | | | |
| 2010/0057042 A1 | 3/2010 | Hayter | | | | |
| 2010/0057044 A1 | 3/2010 | Hayter | | | | |
| 2010/0057057 A1 | 3/2010 | Hayter et al. | | | | |
| 2010/0234710 A1 | 9/2010 | Budiman et al. | | | | |

FOREIGN PATENT DOCUMENTS

| | | |
|---|---|---|
| EP | 0098592 | 1/1984 |
| EP | 0127958 | 12/1984 |

OTHER PUBLICATIONS

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.
PCT Application No. PCT/US2009/058895, International Preliminary Report on Patentability mailed Apr. 14, 2011.
Georgescu, B., et al., "Real-Time Multimodel Tracking of Myocardium in Echocardiography Using Robust Information Fusion", *Medical Image Computing and Computer-Assisted Intervention*, 2004, pp. 777-785.
Goldman, J. M., et al., "Masimo Signal Extraction Pulse Oximetry", *Journal of Clinical Monitoring and Computing*, vol. 16, No. 7, 2000, pp. 475-483.
Maher, "A Method for Extrapolation of Missing Digital Audio Data", *Preprints of Papers Presented at the AES Convention*, 1993, pp. 1-19.
Maher, "Audio Enhancement using Nonlinear Time-Frequency Filtering", *AES 26th International Conference*, 2005, pp. 1-9.
Whipple, G., "Low Residual Noise Speech Enhancement Utilizing Time-Frequency", *Proceedings of the International Conference on Acoustics, Speech, and Signal Processing*, vol. 19, 1994, pp. 15-18.
Wolfe, P. J., et al., "Interpolation of Missing Data Values for Audio Signal Restoration Using a Gabor Regression Model", *2005 IEEE International Conference on Acoustics, Speech, and Signal Processing*, vol. 5, 2005, pp. 517-520.

\* cited by examiner

OPTIMIZING ANALYTE SENSOR CALIBRATION

TECHNICAL FIELD

The present disclosure relates to analyte monitoring devices and systems. More specifically, the present disclosure relates to optimizing calibration of analyte sensors in analyte monitoring devices and systems.

BACKGROUND

There are significant therapeutic advantages for continuously monitoring analyte levels such as glucose levels of diabetic patients. Commercially available continuous glucose monitoring systems use analyte sensors that detect the glucose levels of the patients for a predetermined time period. During this time period, the analyte sensor is generally required to be periodically calibrated with a blood glucose measurement using, for example, an in vitro blood glucose meter.

Calibration of an analyte sensor typically follows a calibration schedule over the life of the analyte sensor, and are intended to maintain the accuracy of the analyte sensor during its useful life. Each calibration routine requires analysis of data from the analyte sensor in conjunction with a reference value, such as from a finger prick test using a lancing device in conjunction with a conventional blood glucose meter. While other areas of the body may be used to perform the blood glucose measurement, such measurement typically requires drawing a blood sample from the patient and applying the blood sample to a blood glucose test strip. This is often a painful experience and which must be performed periodically based on the calibration schedule of the analyte sensor.

SUMMARY

In accordance with the various embodiments of the present disclosure, there are provided method and apparatus for receiving a current blood glucose measurement, retrieving a time information for an upcoming scheduled calibration event for calibrating an analyte sensor, determining temporal proximity between the current blood glucose measurement and the retrieved time information for the upcoming calibration event, and initiating a calibration routine to calibrate the analyte sensor when the determined temporal proximity is within a predetermined time period.

In another aspect, method and apparatus include receiving a current reference data associated with a monitored analyte level, determining whether a next scheduled calibration event for calibrating an analyte sensor associated with the monitored analyte level is within a predetermined time period, validating one or more conditions associated with the calibration of the analyte sensor when the next scheduled calibration event is determined to be within the predetermined time period, and calibrating the analyte sensor based on the received current reference data.

In still a further aspect, an apparatus includes one or more processors; and a memory operatively coupled to the one or more processors for storing instructions which, when executed by the one or more processors, retrieves a time information for an upcoming scheduled calibration event for calibrating an analyte sensor when a current blood glucose measurement is received, determines a temporal proximity between the current blood glucose measurement and the retrieved time information for the upcoming calibration event, and initiates a calibration routine to calibrate the analyte sensor when the determined temporal proximity is within a predetermined time period.

These and other objects, features and advantages of the present disclosure will become more fully apparent from the following detailed description of the embodiments, the appended claims and the accompanying drawings.

DETAILED DESCRIPTION

Figure 1:
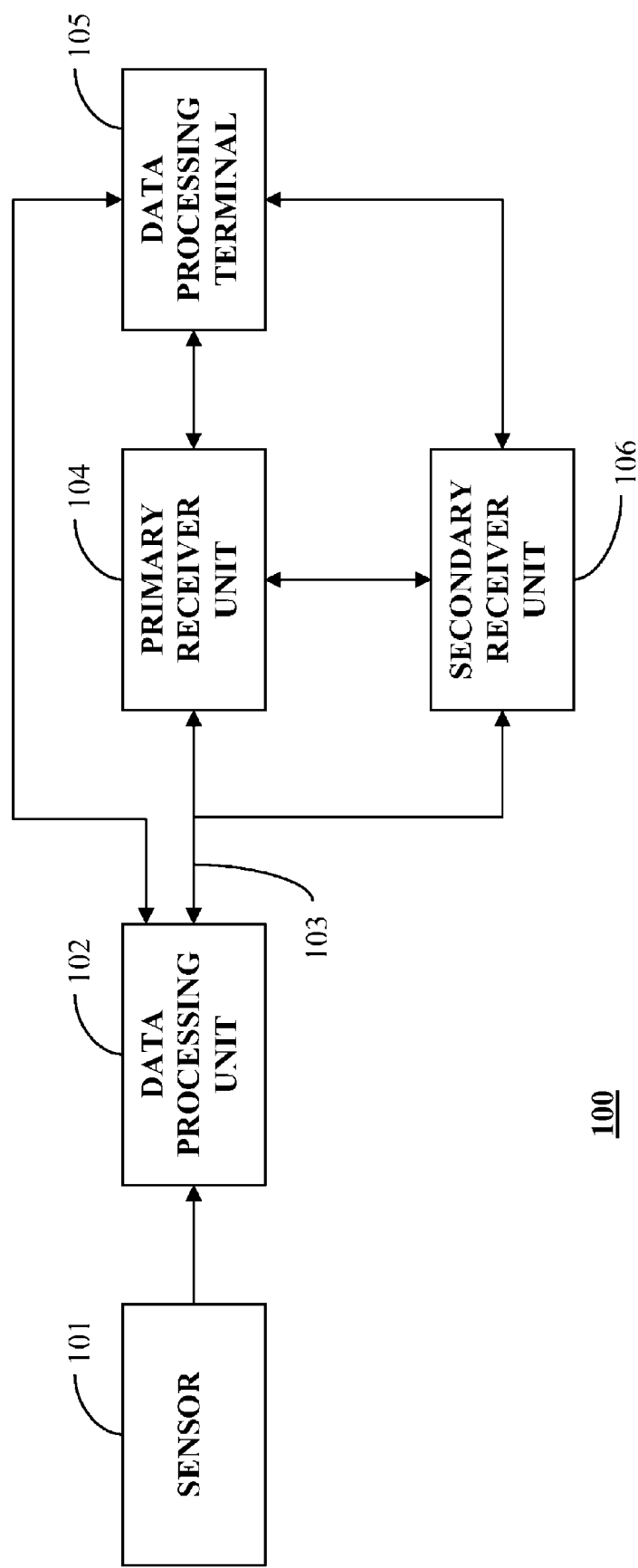
FIG. 1 is a block diagram illustrating an overall system for practicing one or more embodiments of the present disclosure.

Before the present disclosure is described, it is to be understood that this invention is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such pubilication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. In certain embodiments, the present disclosure relates to the continuous and/or automatic in vivo monitoring of the level of an analyte using an analyte sensor.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise.

The analyte level may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject invention may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time $t_0$, the rate of change of the analyte, etc. Predictive alarms may notify the user of predicted analyte levels that may be of concern prior in advance of the analyte level reaching the future level. This enables the user an opportunity to take corrective action.

As described in detail below, in accordance with the various embodiments of the present disclosure, there are provided method, apparatus and system for optimizing analyte sensor calibration to minimize the number of blood glucose measurements in conjunction with the sensor calibration schedule while maintaining the integrity of sensor accuracy.

FIG. 1 shows a data monitoring and management system such as, for example, an analyte (e.g., glucose) monitoring system 100 in accordance with certain embodiments. Embodiments of the subject invention are further described primarily with respect to glucose monitoring devices and systems, and methods of glucose detection, for convenience only and such description is in no way intended to limit the scope of the invention. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 in one embodiment includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique identification codes (IDs), communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including and RF receiver and an antenna that is configured to communicate with the data processing unit 102 via the communication link 103, data processing unit 102 and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring back to FIG. 1, each of the primary receiver unit 104 and the secondary receiver unit 106 may include a blood glucose test strip port such that the user or the patient may perform finger prick tests using blood glucose test strips. Accordingly, in aspects of the present disclosure, the primary receiver unit 104 and the secondary receiver unit 106 may incorporate the functionalities of a blood glucose meter for processing a blood sample to determine a corresponding blood glucose measurement which may be performed by one or more controllers provided in the receiver unit including, for example, a microprocessor, application specific integrated circuit and/or a state machine for executing one or more routines associated with the processing and determination of blood glucose sample to determine the blood glucose level.

Exemplary analyte systems including calibration of analyte sensors that may be employed are described in, for example, U.S. Pat. Nos. 6,134,461, 6,175,752, 6,121,611, 6,560,471, 6,746,582, 7,299,082 and in application Ser. No. 10/745,878 filed Dec. 26, 2003 entitled "Continuous Glucose Monitoring System and Methods of Use", the disclosures of each of which are herein incorporated by reference.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone, Palm® device, Blackberry® device or similar device), mp3 player, pager, and the like), drug delivery device, each of which may be configured for data communication with the receiver via a wired or a wireless connection. Additionally, the data processing terminal 105 may further be connected to a data network (not shown) for additionally storing, retrieving, updating, and/or analyzing data corresponding to the detected analyte level of the user.

In certain embodiments, the communication link 103 as well as one or more of the other communication interfaces shown in FIG. 1 to communicate data between the data processing unit 102, the primary receiver unit 104, secondary receiver unit 106 and the data processing terminal 105 may use one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Furthermore, data communication between the primary receiver unit 104 and the data processing terminal 105, or between the secondary receiver unit 106 and the data processing terminal 105 may include wireless or wired connection such as USB connection, RS-232 connection, serial connection, and the like, to transfer data between the one or more of the primary and the secondary receiver units 104, 106 to the data processing terminal 105.

Figure 2:
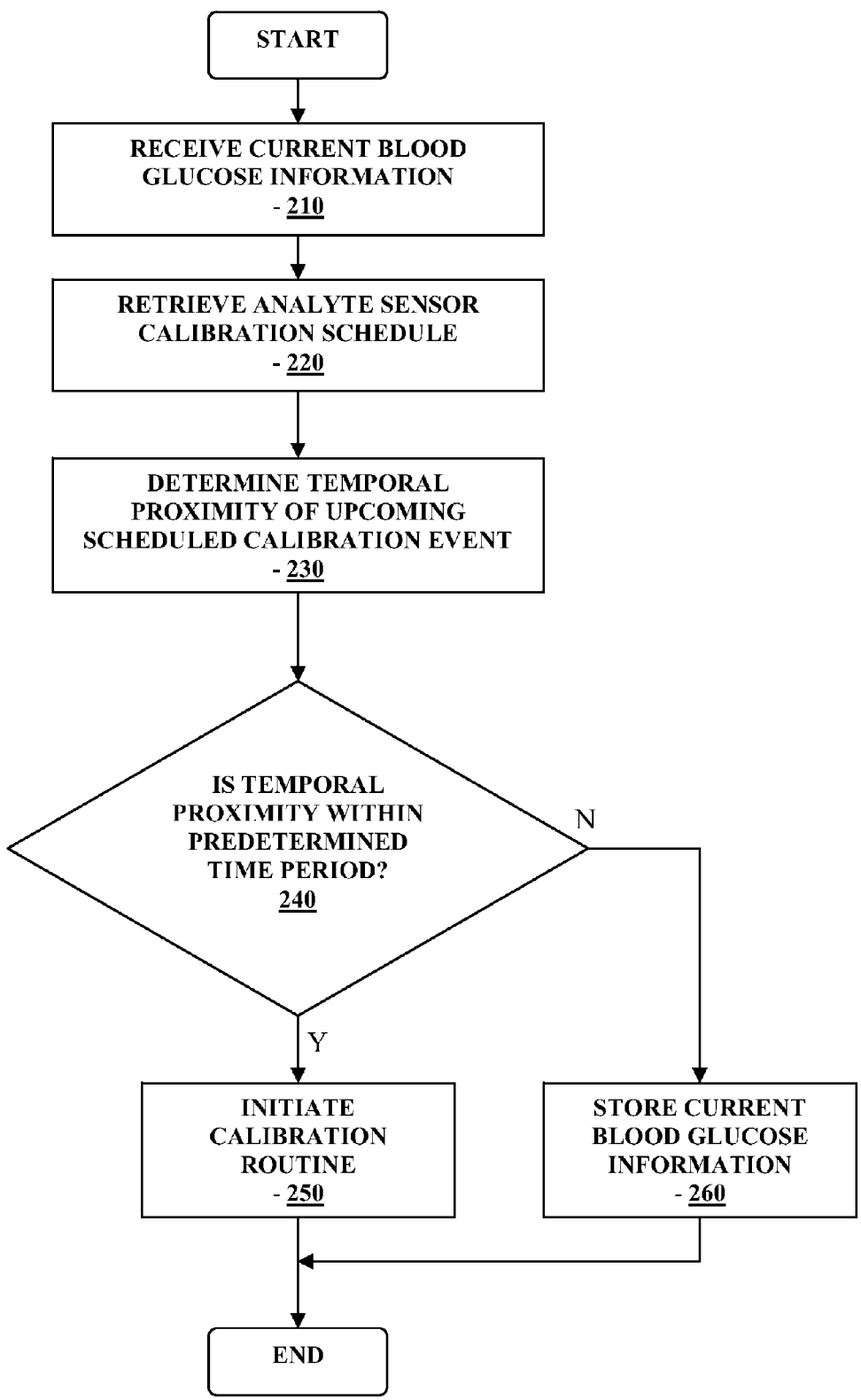
FIG. 2 is an example flowchart for optimizing analyte sensor calibration in accordance with one embodiment of the present disclosure.

FIG. 2 is an example flowchart for optimizing analyte sensor calibration in accordance with one embodiment of the present disclosure. Referring to FIG. 2, in one aspect, when a blood glucose information is received (210) for example, using a finger prick test using a blood glucose test strip, an analyte sensor calibration schedule associated with the analyte sensor 101 (FIG. 1) is retrieved (220). In one aspect, the calibration schedule may include a predetermined time intervals at which the sensor 101 is calibrated using a reference measurement such as a blood glucose measurement. In one aspect, one or more memory module or storage unit of the receiver unit 104/106 may store the calibration schedule associated with the sensor 101.

Referring back to FIG. 2, with the retrieved analyte sensor calibration schedule, a temporal proximity of the next upcoming scheduled calibration event is determined (230). That is, in one aspect, when a blood glucose measurement is received, the sensor calibration schedule is reviewed to determine when the next scheduled calibration event is to occur. Thereafter, the temporal proximity is compared to a predetermined time period to determine whether the timing of when the current blood glucose measurement is within a time window associated with the next scheduled calibration event (240).

For example, given an exemplary calibration schedule of 10 hours, 12 hours, 24 hours and 72 hours measured from the analyte sensor positioning in the patient, when the reference blood glucose measurement is received at the $23^{rd}$ hour from when the sensor was positioned in the patient, the temporal proximity is determined to be approximately one hour from the next scheduled calibration event (at the 24 hour). The temporal proximity is then compared to the predetermined time period which may be pre-programmed, for example, in the receiver unit (104/106) and may include, for example 90 minutes.

That is, in the example provided above, when a blood glucose measurement is received not in response to an execution of a calibration routine to calibrate the sensor 101, it is determined whether the timing of the received blood glucose measurement is within the predetermined time period from the next scheduled calibration event. Referring back to FIG. 2, if it is determined that the temporal proximity of the upcoming or next scheduled calibration event is within the predetermined time period, then the calibration routine to calibrate the analyte sensor is initiated (250).

In one embodiment, when the calibration routine is initiated, a preliminary check, the calibration conditions are evaluated to determine if calibration of the analyte sensor is appropriate, and when it is determined that the calibration conditions are appropriate, the routine proceeds with executing one or more functions associated with the calibration of the analyte sensor. Moreover, as part of the calibration routine, when initiated, the current blood glucose information as well as other data or information may be stored in a memory or storage unit of the receiver unit 104/106.

Referring back to FIG. 2, on the other hand, if it is determined that the temporal proximity is not within the predetermined time period (240), the current blood glucose measurement received is stored, for example, in a memory or storage unit of the receiver unit 104/106 (260). Additionally, the user or the patient may be notified of the successful calibration event, and further, that the successful calibration event overrides the upcoming scheduled calibration, and that the user or the patient will not be prompted or requested to perform the upcoming scheduled calibration including providing another blood glucose information.

In this manner, in one aspect, when the patient or the user of the analyte monitoring system 100 (FIG. 1) performs a blood glucose measurement between the scheduled calibration time periods, a determination is made to accept the blood glucose measurement to perform calibration of the analyte sensor 101. Thereafter, the upcoming or next scheduled calibration event may be overridden or updated with the calibration performed based on the blood glucose measurement received.

Accordingly, additional flexibility and robustness may be provided in the analyte monitoring system 100 while minimizing the number of blood glucose measurements to calibrate the analyte sensor 101 during its useful life. In other words, when the patient or the user of the analyte monitoring system 100 performs a self-initiated blood glucose measurement (for example, using a standard blood glucose meter, or using the receiver unit 104/106 having such functionality integrated therein), in one aspect, it is determined whether the blood glucose measurement may be used to perform calibration of the analyte sensor, and in which case, the next scheduled calibration event may be overridden or not performed as the conditions are such that the calibration routine using the received current blood glucose measurement may replace the upcoming scheduled calibration event.

By way of an example, there may be circumstances where patient motivated blood glucose measurements are performed sufficiently close to the next scheduled calibration of the analyte sensor 101 such that the next scheduled calibration event may be replaced with the calibration routine performed based on the patient motivated blood glucose measurements. Accordingly, in one aspect, the patient or the user of the analyte monitoring system 100 may be subject to one less finger prick test to determine blood glucose measurement to calibrate the analyte sensor 101.

While particular examples are provided above for the predetermined time period used to compare the temporal proximity of the current blood glucose measurement to the next or upcoming scheduled calibration event, and further, while particular example calibration schedule is described above, within the scope of the present disclosure, the particular predetermined time period to compare the temporal proximity of the blood glucose measurement, or the particular calibration schedule may be varied. For example, the calibration schedule may be provided to require calibration routine once every 24 hours measured from the initial sensor insertion. Alternatively, the calibration schedule time periods may be different for each period during the life of the sensor (which may be 3 days, 5 days, 7 days or more), and further, each subsequent calibration routine after the initial calibration may be determined relative to the immediately preceding successful calibration routine performed, and not relative to the time associated with the initial sensor insertion. Moreover, the predetermined time period used to compare the temporal proximity may include other time periods such as approximately one hour, or approximately two hours, or any other suitable time period rather than approximately 90 minutes.

Figure 3:
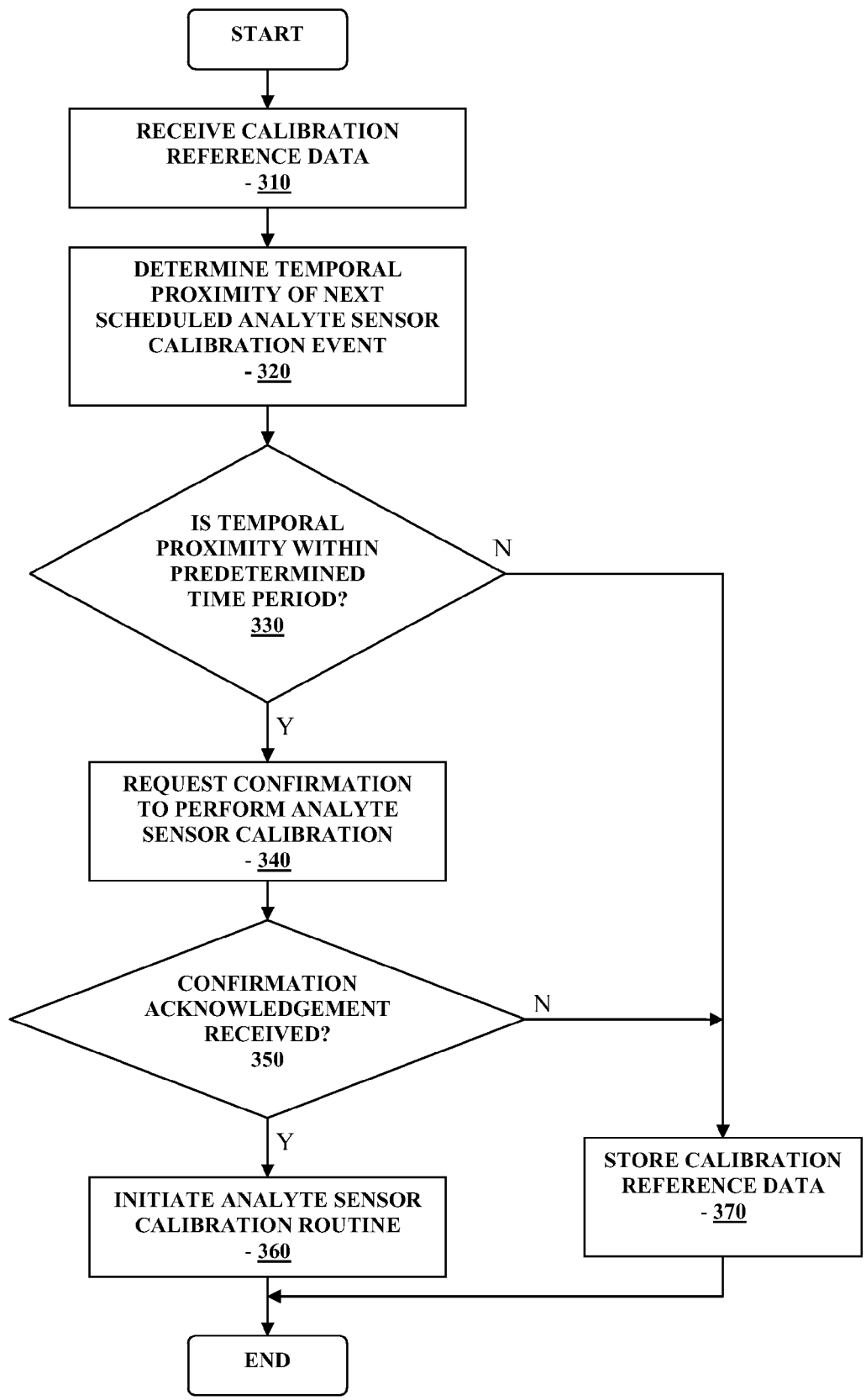
FIG. 3 is an example flowchart for optimizing analyte sensor calibration in accordance with another embodiment of the present disclosure.

FIG. 3 is an example flowchart for optimizing analyte sensor calibration in accordance with another embodiment of the present disclosure. Referring to FIG. 3, in a further aspect, after receiving calibration reference data (310), temporal proximity of the next scheduled analyte sensor calibration event is determined (320). Thereafter, the determined temporal proximity is compared to a predetermined time period as described above (330), and when it is determined that the temporal proximity is not within the predetermined time period, the received calibration reference data is stored (370) and the routine terminates.

On the other hand, referring back to FIG. 3, when it is determined that the temporal proximity of the next scheduled analyte sensor calibration event is within the predetermined time period (relative to when the calibration reference data is received, for example), a request to confirm analyte sensor calibration may be generated and provided to the user or the patient (340). In this manner, the user or the patient may be provided with an opportunity to accept or decline the execution of the calibration routine based on the calibration reference data given the temporal proximity of the next or subsequent upcoming calibration schedule to calibrate the analyte sensor 101 (FIG. 1).

In one aspect, using an output device such as a display on the receiver unit 104/106, the user may be prompted to confirm the execution of the calibration routine in addition to providing information associated with when the next scheduled calibration is to occur. Referring yet again to FIG. 3, when user confirmation acknowledgement is not received (350), then the calibration reference data is stored (370) and the routine terminates. On the other hand, if the user confirmation acknowledgement is received (350), then the analyte sensor calibration routine is initiated (360) to execute the routine associated with the calibration of the analyte sensor. As discussed above, as part of the initiated calibration routine, the calibration reference data as well as other information and data may be stored in the memory or storage device of the receiver unit 104/106.

Referring back to FIG. 3, in a further aspect, when it is determined that the temporal proximity of the next scheduled analyte sensor calibration event is within the predetermined time period, prior to sending the request to confirm the calibration event, calibration conditions may be evaluated to determine whether analyte sensor calibration conditions are appropriate. Alternatively, evaluation of the calibration conditions may be performed after the user or the patient has provided acknowledgement confirmation to perform the calibration.

As discussed in further detail below, initiating the calibration routine may include, in one aspect, validating or confirming the acceptability of the received calibration reference data (for example, a determination that the blood glucose measurement used as the calibration reference data is within a predefined acceptable range such as 40 mg/dL to 400 mg/dL). Additionally, conditions or parameters associated with the execution of the calibration routine may be performed including, for example, determining the rate of the change of the analyte level to be within an acceptable range for calibration, the temperature information associated with the analyte sensor is within an acceptable range, or there are a sufficient number of analyte sensor data points to perform calibration.

Figure 4:
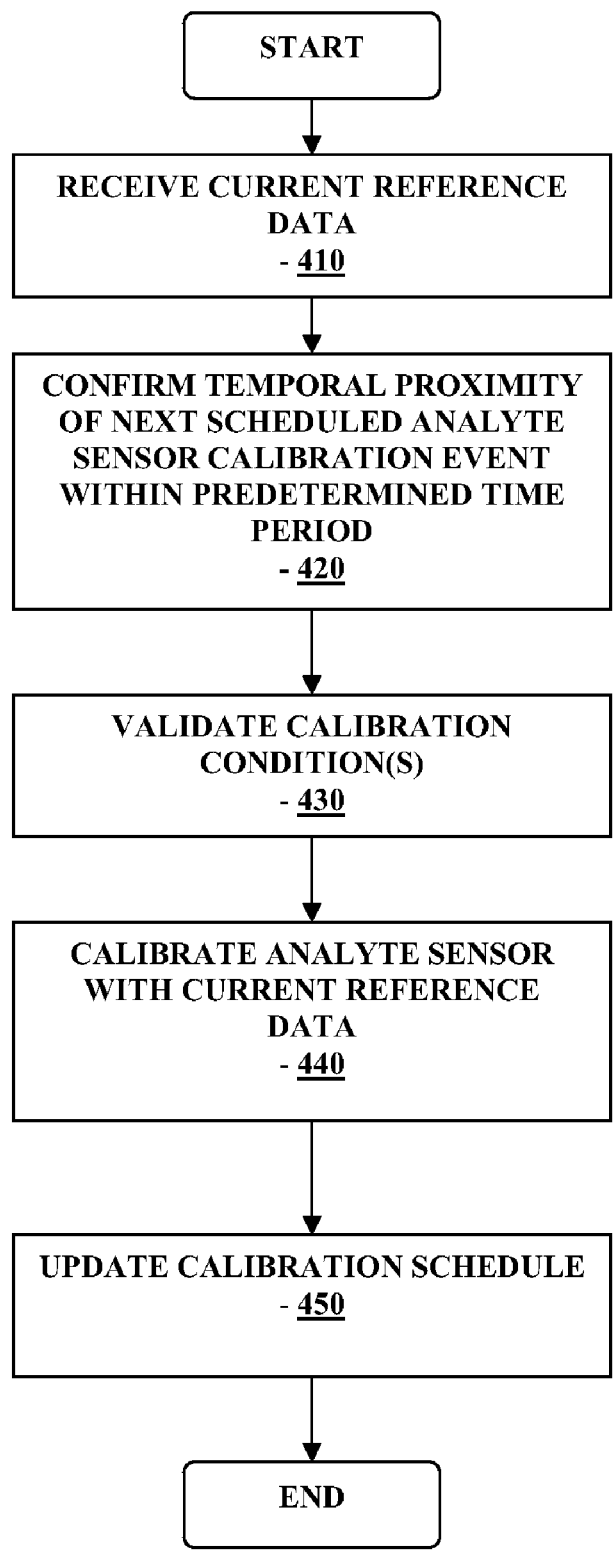
FIG. 4 is an example flowchart for optimizing analyte sensor calibration in accordance with yet another embodiment of the present disclosure.

FIG. 4 is an example flowchart for optimizing analyte sensor calibration in accordance with yet another embodiment of the present disclosure. Referring to FIG. 4, in one aspect, when the current reference data is received (410), temporal proximity of the next scheduled analyte sensor calibration event is confirmed to be within a predetermined time period (for example, such as 90 minutes from when the current reference data is received) (420). Thereafter, calibration conditions are validated to determine that conditions associated with the patient and the analyte sensor, among others, are appropriate (430).

For example, in one aspect, the calibration condition may not be valid when the rate of change of the analyte level exceeds a predetermined threshold level or range. In another aspect, the calibration condition may be determined to be invalid when insufficient analyte sensor data points are present (whether due to data packet drop outs from the data processing unit 102 (FIG. 1), or signal dropout events such as signal attenuation. Within the scope of the present disclosure, other parameters and/or conditions are reviewed and analyzed to determine whether the calibration condition is valid. Examples of such other parameters or conditions are further described in U.S. Pat. Nos. 6,175,752 and 7,299,083, among others, the disclosure of each of which are incorporated by reference for all purposes.

Referring back to FIG. 4, upon validation of the calibration conditions (430), the analyte sensor is calibrated using the received current reference data (440). Moreover, after calibration, the stored calibration schedule in one aspect may be retrieved and updated to include the calibration performed based on the received current reference data (450). Moreover, in one aspect, the retrieved calibration schedule may be updated to replace the next scheduled analyte sensor calibration event with the calibration based on the current reference data.

In the manner provided, within the scope of the present disclosure, using the non-calibration prompted and user initiated blood glucose measurements, under certain conditions such as time proximity to the subsequent scheduled calibration event, among others, the number of required blood glucose measurement using a blood glucose test strip may be minimized.

Referring still to the various embodiments of the present disclosure, as discussed above, the analyte monitoring system may automatically perform the calibration of the analyte sensor based on the blood glucose measurement received, and thereafter, notify the user or the patient of the successful calibration of the sensor, or alternatively, provide the patient or the user with the option to confirm the performance of the calibration of the sensor based on the receive blood glucose measurement. Within the scope of the present disclosure, other variations or levels of user or patient interaction may be contemplated, such as, for example, notification (alarms or alerts that are visual, auditory, vibratory or one or more combinations thereof) to the user of calibration associated events such as updating the previously stored calibration schedule based on the calibration performed with the current reference or blood glucose data, notification of the next valid scheduled calibration, the number of calibrations remaining for the sensor prior to sensor replacement, failed calibration attempt, unsuitable calibration conditions, verified valid calibration conditions, and the like.

Accordingly, a method in one aspect includes receiving a current blood glucose measurement, retrieving a time information for an upcoming scheduled calibration event for calibrating an analyte sensor, determining temporal proximity between the current blood glucose measurement and the retrieved time information for the upcoming calibration event, and initiating a calibration routine to calibrate the analyte sensor when the determined temporal proximity is within a predetermined time period.

In one aspect, initiating the calibration routine may include calibrating the analyte sensor based on the received current blood glucose measurement.

Moreover, the method may include determining validity of the current blood glucose measurement, for example, by comparing the current blood glucose measurement to a predetermined ranges or values.

Additionally, determining validity of the current blood glucose measurement may include analyzing the current blood glucose measurement based on a predetermined threshold range, a temperature information, or a combination thereof.

In still another aspect, the method may include determining the validity of an analyte sensor data, including one or more of analyzing the analyte sensor data based on one or more of a rate of change of the analyte level, a temperature information, a predetermined analyte level threshold range, or one or more combinations thereof.

In another aspect, the method may include overriding the upcoming scheduled calibration event when the calibration routine to calibrate the analyte sensor based on the received current blood glucose measurement is successful.

Also, initiating the calibration routine may include validating one or more calibration condition parameters associated with the calibration of the analyte sensor.

Yet still further aspect may include generating an output signal confirming completion of the upcoming scheduled calibration event.

In yet another aspect, the method may include updating a calibration schedule for calibrating the analyte sensor based on the initiated calibration routine.

Further, initiating calibration routine may include automatically performing the calibration routine to calibrate the analyte sensor when the determined temporal proximity is within the predetermined time period.

A method in accordance with another aspect of the present disclosure includes receiving a current reference data associated with a monitored analyte level, determining whether a next scheduled calibration event for calibrating an analyte sensor associated with the monitored analyte level is within a predetermined time period, validating one or more conditions associated with the calibration of the analyte sensor when the next scheduled calibration event is determined to be within the predetermined time period, and calibrating the analyte sensor based on the received current reference data.

The analyte sensor may be associated with a time spaced calibration schedule including the next scheduled calibration event.

The time spaced calibration schedule may include unevenly time spaced calibration schedule during the life of the sensor.

In another aspect, the method may include updating the time spaced calibration schedule based on analyte sensor calibration using the received current reference data Also, the method may include associating the current reference data with a corresponding calibrated analyte sensor data.

Additionally, in a further aspect, the method may include disabling a calibration routine associated with the next scheduled calibration event.

An apparatus in accordance with another aspect of the present disclosure includes one or more processors, and a memory operatively coupled to the one or more processors for storing instructions which, when executed by the one or more processors, retrieves a time information for an upcoming scheduled calibration event for calibrating an analyte sensor when a current blood glucose measurement is received, determines a temporal proximity between the current blood glucose measurement and the retrieved time information for the upcoming calibration event, and initiates a calibration routine to calibrate the analyte sensor when the determined temporal proximity is within a predetermined time period.

The apparatus may include a blood glucose strip port configured to receive a blood glucose test strip providing the current blood glucose measurement. That is, in one aspect, the receiver unit 104/106 (FIG. 1) may include an integrated blood glucose test strip port and configured to analyze the blood sample received from the test strip to determine the corresponding blood glucose level.

In still another aspect, the apparatus may include a housing coupled to the blood glucose strip port and further, wherein the one or more processors and the memory are provided in the housing.

The various processes described above including the processes performed by the one or more processors of the receiver unit 104/106, or optionally the data processing unit 102 (FIG. 1), in the software application execution environment as well as any other suitable or similar processing units embodied in the analyte monitoring system 100, including the processes and routines described in conjunction with FIGS. 2-4, may be embodied as computer programs developed using an object oriented language that allows the modeling of complex systems with modular objects to create abstractions that are representative of real world, physical objects and their interrelationships. The software required to carry out the inventive process, which may be stored in a memory (or similar storage devices in the data processing unit 102, or the receiver unit 104/106) of the processor, may be developed by a person of ordinary skill in the art and may include one or more computer program products.

Various other modifications and alterations in the structure and method of operation of this present disclosure will be apparent to those skilled in the art without departing from the scope and spirit of the present disclosure. Although the present disclosure has been described in connection with specific preferred embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. A method, comprising:
receiving a reference blood glucose measurement obtained from a test strip;
retrieving, using one or more processors, a time information for an upcoming scheduled calibration event for calibrating an analyte sensor;
determining, using the one or more processors, temporal proximity between the reference blood glucose measurement and the retrieved time information for the upcoming calibration event; and
initiating, using the one or more processors, a calibration routine to calibrate the analyte sensor when the determined temporal proximity is within a predetermined time period.

2. The method of claim 1 wherein initiating the calibration routine includes calibrating the analyte sensor based on the received reference blood glucose measurement.

3. The method of claim 2 including determining, using the one or more processors, validity of the reference blood glucose measurement.

4. The method of claim 3 wherein determining validity of the reference blood glucose measurement includes analyzing the reference blood glucose measurement based on a predetermined threshold range, a temperature information, or a combination thereof.

5. The method of claim 2 including determining, using the one or more processors, the validity of an analyte sensor data.

6. The method of claim 5 wherein determining the validity of the analyte sensor data includes one or more of analyzing the analyte sensor data based on one or more of a rate of change of an analyte level, a temperature information, a predetermined analyte level threshold range, or one or more combinations thereof.

7. The method of claim 2 including overriding the upcoming scheduled calibration event when the calibration routine to calibrate the analyte sensor based on the received reference blood glucose measurement is successful.

8. The method of claim 1 wherein initiating the calibration routine includes validating one or more calibration condition parameters associated with the calibration of the analyte sensor.

9. The method of claim 1 including generating an output signal confirming completion of the upcoming scheduled calibration event.

10. The method of claim 1 including updating a calibration schedule for calibrating the analyte sensor based on the initiated calibration routine.

11. The method of claim 1 wherein initiating the calibration routine includes automatically performing the calibration routine to calibrate the analyte sensor when the determined temporal proximity is within the predetermined time period.

12. A method, comprising:
receiving reference data associated with a monitored analyte level from a test strip;
determining, using one or more processors, whether a next scheduled calibration event for calibrating an analyte sensor associated with the monitored analyte level is within a predetermined time period from the receipt of the reference data;
validating, using the one or more processors, one or more conditions associated with the calibration of the analyte sensor when the next scheduled calibration event is determined to be within the predetermined time period from the receipt of the reference data; and
calibrating, using the one or more processors, the analyte sensor based on the received reference data when the next scheduled calibration event is determined to be within the predetermined time period from the receipt of the reference data.

13. The method of claim 12 wherein the analyte sensor is associated with a time spaced calibration schedule including the next scheduled calibration event.

14. The method of claim 13 wherein the time spaced calibration schedule includes unevenly time spaced calibration schedule during the life of the sensor.

15. The method of claim 13 including updating, using the one or more processors, the time spaced calibration schedule based on analyte sensor calibration using the received reference data.

16. The method of claim 12 including associating, using the one or more processors, the reference data with a corresponding calibrated analyte sensor data.

17. The method of claim 12 including disabling, using the one or more processors, a calibration routine associated with the next scheduled calibration event.

18. An apparatus, comprising:
one or more processors; and
a memory operatively coupled to the one or more processors for storing instructions which, when executed by the one or more processors, retrieves a time information for an upcoming scheduled calibration event for calibrating an analyte sensor when a reference blood glucose measurement is received, determines a temporal proximity between the reference blood glucose measurement and the retrieved time information for the upcoming calibration event, and initiates a calibration routine to calibrate the analyte sensor when the determined temporal proximity is within a predetermined time period.

19. The apparatus of claim 18 including a blood glucose strip port configured to receive a blood glucose test strip providing the reference blood glucose measurement.

20. The apparatus of claim 19 including a housing coupled to the blood glucose strip port and further, wherein the one or more processors and the memory are provided in the housing.

* * * * *